(12) United States Patent
Auer et al.

(10) Patent No.: US 7,440,101 B2
(45) Date of Patent: Oct. 21, 2008

(54) SYSTEM AND METHOD FOR MULTIPLE LASER TRIGGERING

(75) Inventors: Robert Edward Auer, Key Largo, FL (US); Clarence Lew, Irvine, CA (US); Stephen Lyle Pentoney, Chino Hills, CA (US); David Lin Yang, Orange, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 492 days.

(21) Appl. No.: 10/763,652

(22) Filed: Jan. 23, 2004

(65) Prior Publication Data

US 2005/0162648 A1    Jul. 28, 2005

(51) Int. Cl.
*G01N 21/00*    (2006.01)
(52) U.S. Cl. .................... 356/338; 356/317; 350/458.1
(58) Field of Classification Search .................. None
See application file for complete search history.

(56) References Cited

U.S. PATENT DOCUMENTS

| | | | | |
|---|---|---|---|---|
| 4,038,556 | A | | 7/1977 | Auer et al. ............... 250/575 |
| 4,243,318 | A | | 1/1981 | Stöhr ....................... 356/39 |
| 4,284,412 | A | * | 8/1981 | Hansen et al. .......... 250/432 R |
| 4,573,796 | A | * | 3/1986 | Martin et al. ............ 356/318 |
| 4,988,619 | A | * | 1/1991 | Pinkel ..................... 356/73 |
| 5,150,313 | A | * | 9/1992 | van den Engh et al. ... 702/79 |
| 5,367,474 | A | | 11/1994 | Auer et al. ............... 364/555 |
| 5,480,775 | A | | 1/1996 | Ito et al. .................. 435/7.2 |
| 5,483,469 | A | * | 1/1996 | Van den Engh et al. ... 356/336 |
| 5,528,045 | A | | 6/1996 | Hoffman et al. ......... 250/458.1 |
| 5,682,038 | A | | 10/1997 | Hoffman ................. 250/458.1 |

(Continued)

FOREIGN PATENT DOCUMENTS

WO    WO 98/41876    9/1998

(Continued)

OTHER PUBLICATIONS

Steinkamp, John A. et al., "Improved multilaser/multiparameter flow cytometer for analysis and sorting of cells and particles,"*Review of Scientific Instruments*, 62(11);2751-2764 (November 1, 1991).

(Continued)

*Primary Examiner*—Gregory J. Toatly, Jr.
*Assistant Examiner*—Juan D Valentin
(74) *Attorney, Agent, or Firm*—Sterne, Kessler, Goldstein & Fox, P.L.L.C.

(57) ABSTRACT

A system for measuring the irradiance of a fluorescently labeled particle having a cytometric flow chamber; a plurality of excitation light sources; a plurality of scatter detectors, each configured to detect light from only one of the plurality of excitation light sources and arranged so as to detect scattered light from the particle; a trigger connected to the plurality of scatter detectors, the trigger emitting a signal when scattered light incident on one of the scatter detectors is exceeding a predetermined threshold value; collection optics; at least one fluorescence detector to receive emissions collected by the collection optics and generate an output, the at least one fluorescence detector being configured to respond only to a discrete number of wavelength bands; and an integrator for recording the output of the at least one fluorescence detector in response to a signal from the trigger.

8 Claims, 14 Drawing Sheets

U.S. PATENT DOCUMENTS

| | | | |
|---|---|---|---|
| 5,880,474 A | 3/1999 | Norton et al. | 250/458.1 |
| 6,743,634 B2 * | 6/2004 | Kramer | 436/63 |
| 7,064,827 B2 * | 6/2006 | Nurmikko et al. | 356/318 |
| 7,148,492 B2 * | 12/2006 | Loney et al. | 250/458.1 |

FOREIGN PATENT DOCUMENTS

| | | |
|---|---|---|
| WO | WO 98/52018 | 11/1998 |
| WO | WO 03/008937 | 1/2003 |
| WO | WO 03/042695 | 5/2003 |

OTHER PUBLICATIONS

Article, Buying Flow Cytometers, pp. 413-432.

* cited by examiner

SYSTEM AND METHOD FOR MULTIPLE LASER TRIGGERING

BACKGROUND

The present invention relates to flow cytometry, and more particularly, to a system and method for using multiple lasers in flow cytometry.

In a typical flow cytometer 10, as shown in FIG. 1, a sample solution of particles 12 is combined with a sheath fluid 14. The particles may be fluorescently-labeled, and may be cells or microspheres made of polystyrene or other material. The sheath fluid 14 flows in such a way as to hydrodynamically focus the particle containing sample solution 12 for analysis. The particle containing sample solution 12 and the sheath fluid 14 flow along a flow path 16. An excitation light source 18, typically a laser, is focused upon the particles 12 as they flow along the flow path 16 to induce fluorescence from any reporter dyes present in or on the particles. Any fluorescence from the particles is captured via collection optics 20 positioned orthogonal to the path of the laser beam, and detected using a photomultiplier tube 22.

A forward angle light scatter (FALS) detector 24, typically a photodiode or other light detector, is placed just off the laser axis and captures light scattered by the particle. It is the signal from the FALS detector that indicates the presence of the particles and is usually the trigger for data collection. When the amplitude of the FALS detector signal is greater than a predetermined threshold value, indicating the presence of a particle, data collection electronics are triggered and signals generated by the photomultiplier tubes are acquired as either integral and/or peak values.

For a single laser system, alignment of the laser beam to the flow path, as well as alignment for the collection of the scattered light, is straightforward. Typically, alignment involves adjusting the position of the laser beam to maximize the FALS response, then adjusting the collection optics to maximize the fluorescent signal. This process is illustrated in U.S. Pat. No. 4,038,556, the entire contents of which are hereby incorporated herein by reference.

To facilitate multiplexing, a particle may contain one or more encoding dyes that need to be excited by one or more excitation light sources. The use of multiple excitation light sources generally adds an increased level of complexity, because all excitation light sources need to be aligned with respect to the collection optics.

One solution is to align the excitation light sources so that they focus to the same point in the flow chamber. The excitation light sources may be collinear or not, but should coincide in the detection zone. The mutual alignment of the excitation light sources should be performed by observing the forward scatter signal from each of the excitation light sources as particles pass through the flow chamber using an oscilloscope. The positions of the excitation light sources are adjusted until the forward scatter from the excitation light sources coincides in time. This results in the excitation light sources striking the particle at the same location in the flow chamber. This adjustment is often very cumbersome and time consuming, and any relative misalignment of the excitation light sources may cause signal reduction for one or more fluorescent channels.

It is often desirable to separate the excitation light sources so that each particle passes sequentially through each excitation light source. Separation of the excitation light sources results in a spatial separation in the signals from the particles, which facilitates the capture of the specific responses of the particles to separate excitation sources. However, separation of the excitation light sources adds increased complexity, because the signals are temporally separate. An example of a system employing separated lasers is disclosed in U.S. Pat. No. 4,243,318, the entire contents of which are hereby incorporated herein by reference.

Alternative solutions to temporal separation, such as the use of gated amps or delay lines, require preexisting knowledge of the relative separation of the excitation light sources and cannot correct for excitation light source or core velocity drift during the course of an experiment. Examples of alternative solutions are shown in U.S. Pat. Nos. 5,528,045, 5,682,038, 5,880,474, and Beckman Coulter EPIC 750 and Beckman Coulter ELITE Manuals, the contents of which are hereby incorporated herein by reference.

There is therefore a need for an improved method of aligning two or more excitation light sources with particles in a flow chamber.

SUMMARY

Accordingly, the present invention is directed to a system for measuring the irradiance of a fluorescently labeled particle. The system includes a cytometric flow chamber having a flow path for passage of the fluorescently labeled particle. The system also has a plurality of excitation light sources, each emitting a beam of light incident on the cytometric flow chamber. A plurality of scatter detectors are in optical communication with the flow path of the cytometric flow chamber, each configured to detect light from only one of the plurality of excitation light sources and arranged so as to detect scattered light from the fluorescently labeled particle as it passes through the flow path of the cytometric flow chamber.

A trigger is connected to the plurality of scatter detectors. The trigger emits a signal when scattered light incident on one of the scatter detectors is exceeding a predetermined threshold value. Collection optics are in optical communication with the flow path of the cytometric flow chamber, to collect emissions from the fluorescently labeled particle.

At least one fluorescence detector receives the emissions collected by the collection optics and generate outputs. The at least one fluorescence detector is configured to respond only to a discrete band of wavelengths. Electronic integrators are connected to the trigger and the at least one fluorescence detector, for recording the output of the at least one fluorescence detector in response to a signal from the trigger.

Additionally, the present invention is directed to a method for measuring the fluorescence of a particle having a plurality of dyes. The method comprises the steps of interrogating a particle with a first excitation light source; detecting the interrogation of the particle with the first excitation light source using a scatter detector configured to only detect light from the first excitation light source; and detecting any fluorescence emitted by the particle using a fluorescence detector when it is detected that the particle is being interrogated by the first excitation light source.

Additionally, the method comprises the steps of interrogating a particle with a second excitation light source; detecting the interrogation of the particle with the second excitation light source using a scatter detector configured to only detect light from the second excitation light source; and detecting any fluorescence emitted by the particle using a fluorescence detector when it is detected that the particle is being interrogated by the second excitation light source.

Additionally, a system for measuring the irradiance of a fluorescently labeled particle according to the present invention may have a plurality of triggers, each of the plurality of triggers being coupled to a separate scatter detector. The system may also have a plurality of fluorescence detectors. A plurality of integrators may be coupled to the plurality of triggers, each integrator being configured to record the output of at least one of the plurality of fluorescence detectors in response to a signal from a trigger. Optionally, the system has a controller coupled to the plurality of integrators and the plurality of triggers, the controller being programmed to control the plurality of integrators and the plurality of triggers to prevent anomalous data from being acquired.

BRIEF DESCRIPTION OF THE DRAWINGS

A better understanding of the present invention will be had with reference to the accompanying drawings in which.

DETAILED DESCRIPTION

Figure 1:
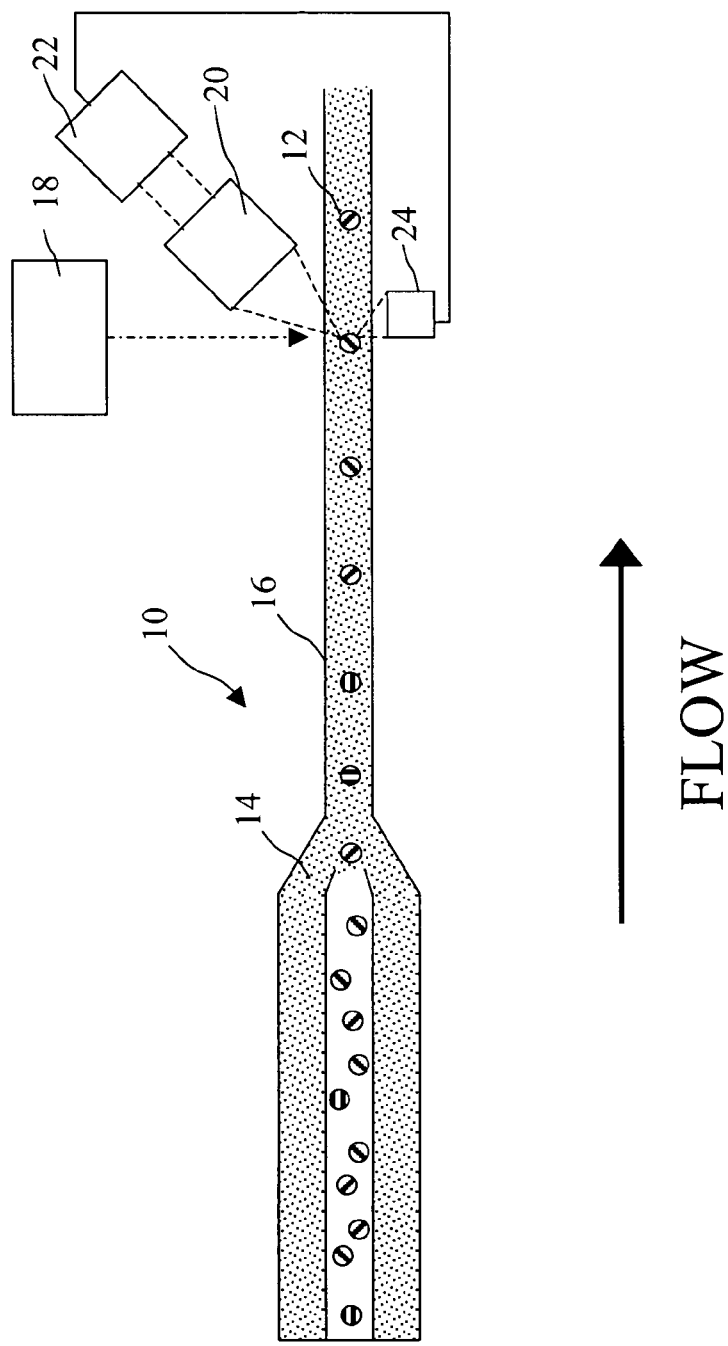
FIG. 1 is a diagram showing a prior art flow cytometry system.

Typically, the present invention is used in conjunction with flow cytometry applications. In flow cytometry, one or more excitation light sources are used to interrogate particles as they pass single file through a detection region of a flow chamber. The sample particles may be microspheres containing and/or coated with fluorescent reporter dyes excited by an excitation light source. Typically, the microsphere is a polystyrene particle having a diameter of 0.5 to 10 µm.

The excitation light source can be a diode laser, a solid state laser, a gas laser, a dye laser, an arc lamp, or other illumination source as known by those skilled in the art. For example, a 532 nm laser may be used to induce fluorescence of dyes such as phycoerythrin (PE), CY3 and DBCY3 dyes at approximately 550 to 620 nm, while a 635 nm laser may be used to induce fluorescence of dyes such as squarine and cyanine dyes at approximately 650 nm to 750 nm. A third laser, emitting at 488 nm, may be included, and the invention disclosed here can be easily extended to more than three lasers. Additional dyes that may be used include fluorescein, Alexa532, and Alexa633. Additional wavelengths of excitation light sources that may be used include 650 nm and 750 nm.

Induced fluorescence is detected by fluorescence detectors. Typically fluorescence detectors are photomultiplier tubes or other detectors as known in the art. The fluorescence detectors are typically coupled to an integrator which collects the signals produced by the fluorescence detectors within a time window. An integrator may be used to not only integrate the entire signal received by a fluorescence detector, but may also be used to record the peak or maximum intensity received by the fluorescence detector.

In the present invention, the need to align and maintain alignment of two or more excitation light sources is minimized by capturing scattered light with two or more scatter detectors. Typically each scatter detector has a photodiode or other known detector. A bandpass filter is placed in front of each photodiode allowing light from only one excitation light source to reach that photodiode. Therefore, when a scatter detector detects scattered light, the particle under investigation is known to be in the path of a beam from a particular excitation light source. The scatter detector signal may trigger data acquisition from the fluorescence detectors associated with a particular excitation light source. Alternatively, the scatter detector signal may trigger data collection from all fluorescence detectors. Typically, data processing occurs after the signals have been passed through delay lines. The use of delay lines is discussed in U.S. Pat. No. 5,367,474, the entire contents of which are hereby incorporated herein by reference.

FIGS. 2 to 9 show a flow cytometer 30 according to one embodiment of the present invention. Three excitation light sources 32, 34, 36 are focused so that each will interrogate a particle 38 at a different point along a flow path 40. Three photodiodes 42, 44, 46, acting as scatter sensors, are sequentially arranged. Each photodiode is optically coupled to a separate bandpass filter 48, 50, 52 allowing light from only one of the excitation light sources to pass through to the photodiode. Additionally, each of the photodiodes 42, 44, 46 has a separate collection lens 54, 56, 58 placed in front it to collect scattered light for detection by the photodiode. Optionally, beam dumps (not shown) block each of the unscattered excitation light source beams and prevent them from entering the collection lens. The photodiodes are electrically coupled to a trigger 60. The trigger 60 is electrically coupled to an integrator 62. The integrator 62 is electrically coupled to a plurality of fluorescence detectors (not shown). The fluorescence detector(s) are positioned out of the direct path of the excitation light source beams. It will be understood by those skilled in the art that each photodiode may be coupled to a separate trigger, each separate trigger may be coupled to a separate integrator, and each separate integrator may be coupled to a separate fluorescence detector.

Figure 2:
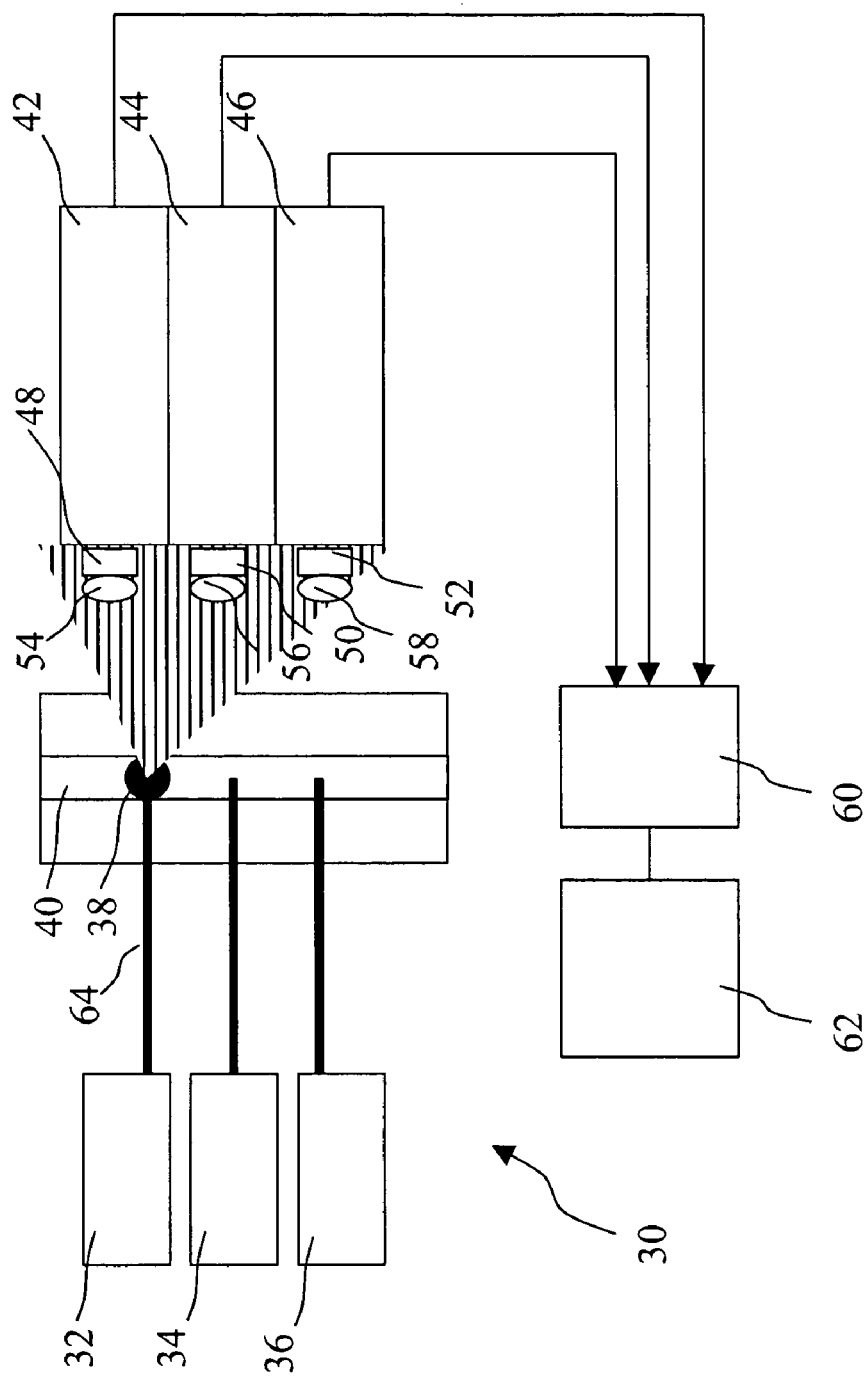
FIG. 2 is a diagram showing a flow cytometry system employing three excitation light sources according to one embodiment of the present invention where a particle is passing through a beam from the first of the three excitation light sources.
Figure 3:
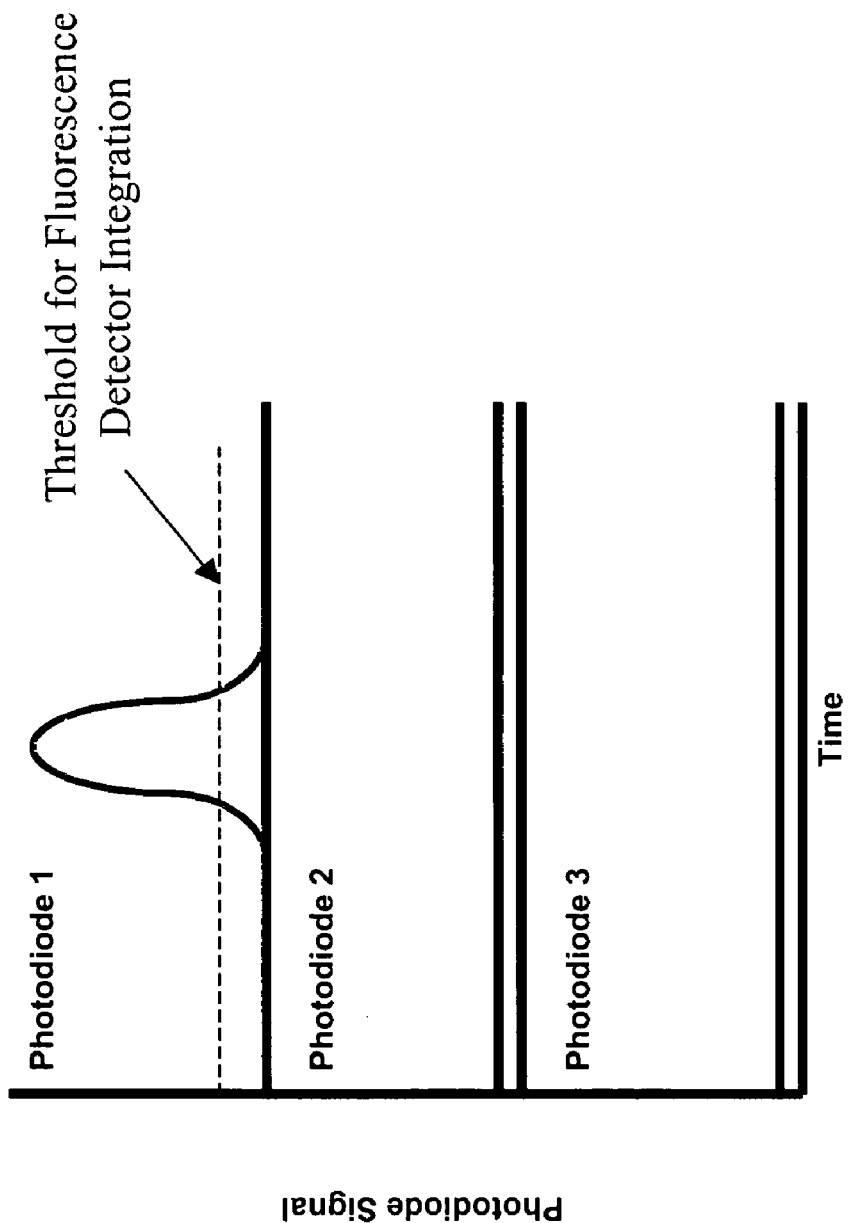
FIG. 3 is a graph showing the signals received from the scatter detectors as illustrated in FIG. 2.

In FIGS. 2 and 3, the particle 38, flowing through the flow path 40, passes through a beam of light 64 from the first excitation light source 32. The first photodiode 42, which is configured with the first band pass filter 48 to only detect light at the wavelength of the first excitation light source 32, detects scattered light. If the amount of scattered light detected is higher than a preselected threshold, then the trigger 60 triggers the integrators 62 to integrate the signals from the fluorescence detectors associated with the dyes excited by the first excitation light source 32. The second and third photodiodes 44, 46, which are configured to detect scattered light from the second and third excitation light sources 34, 36, do not detect any light.

Figure 4:
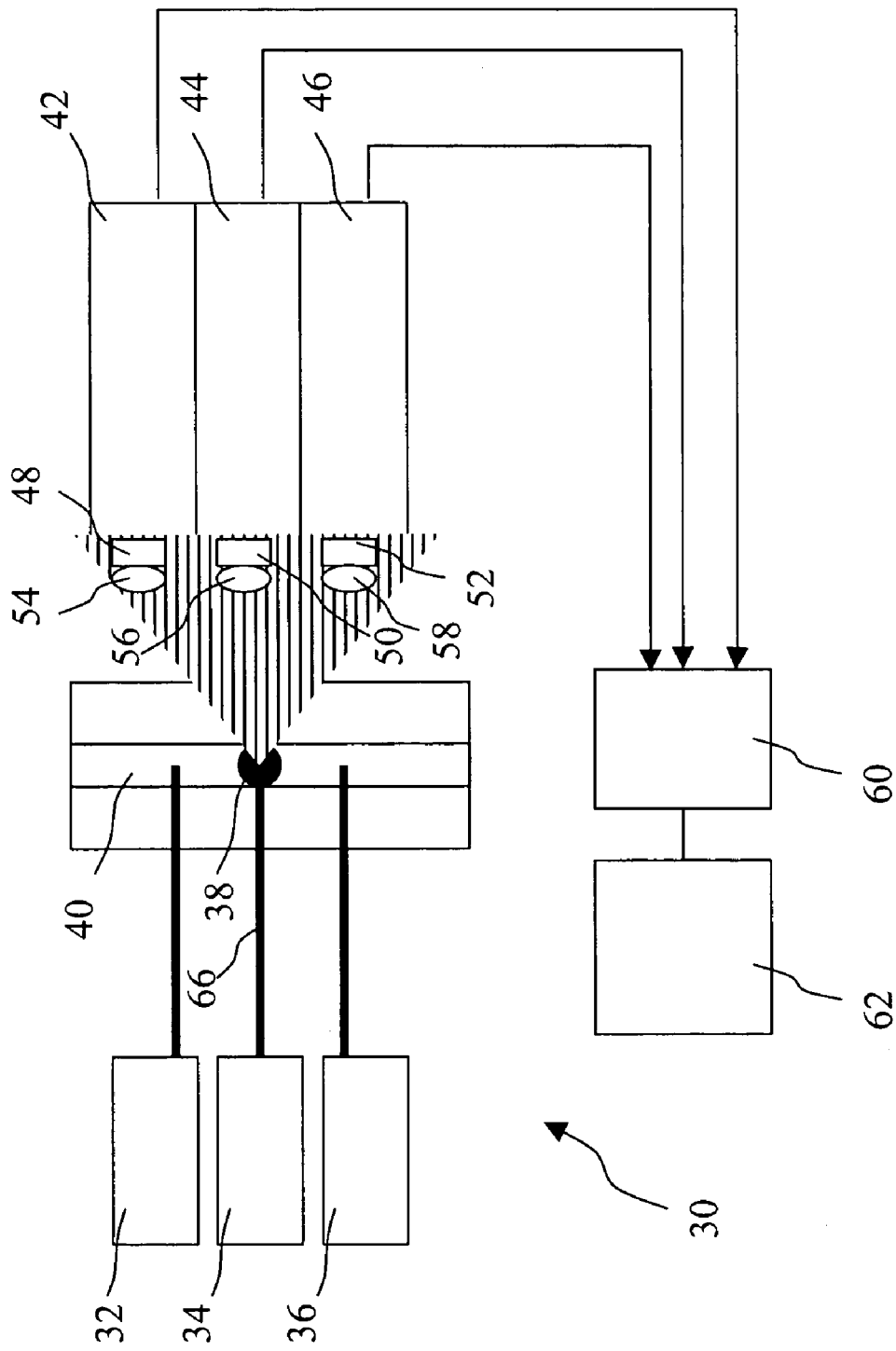
FIG. 4 is a diagram showing the cytometry system of FIG. 2 where a particle is passing through a beam from the second of the three excitation light sources.
Figure 5:
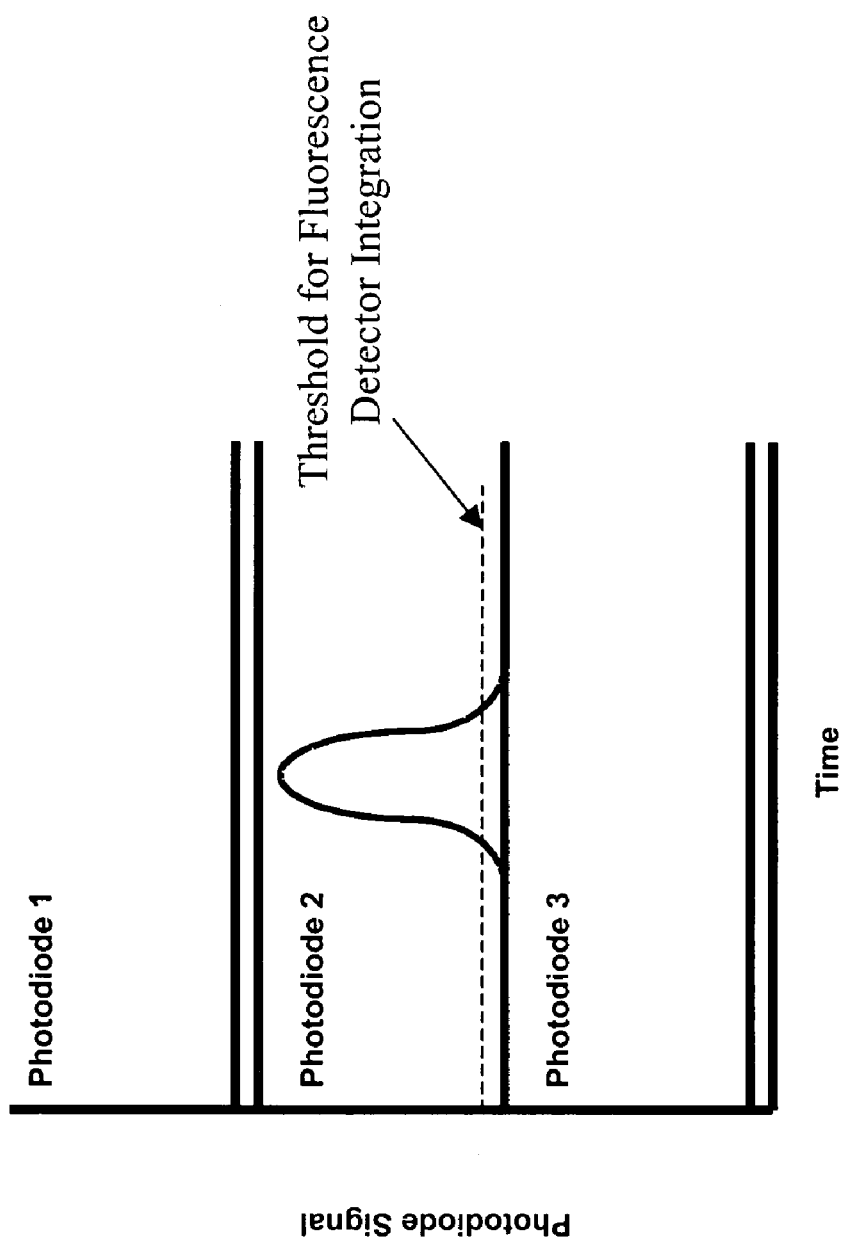
FIG. 5 is a graph showing the signals received from the scatter detectors as illustrated in FIG. 4.

In FIGS. 4 and 5, the particle 38 passes through a beam of light 66 from the second excitation light source 34. The second photodiode 44, which is configured with the second band pass filter 50 to only detect light at the wavelength of the second excitation light source 34, detects scattered light. If the amount of scattered light detected is higher than a preselected threshold, then the trigger 60 triggers the integrators 62 to integrate the signals from the fluorescence detectors associated with the dyes excited by the second excitation light source 34. The first and third photodiodes 42, 46, which are configured to detect scattered light from the first and third excitation light sources 32, 36, do not detect any light.

Figure 6:
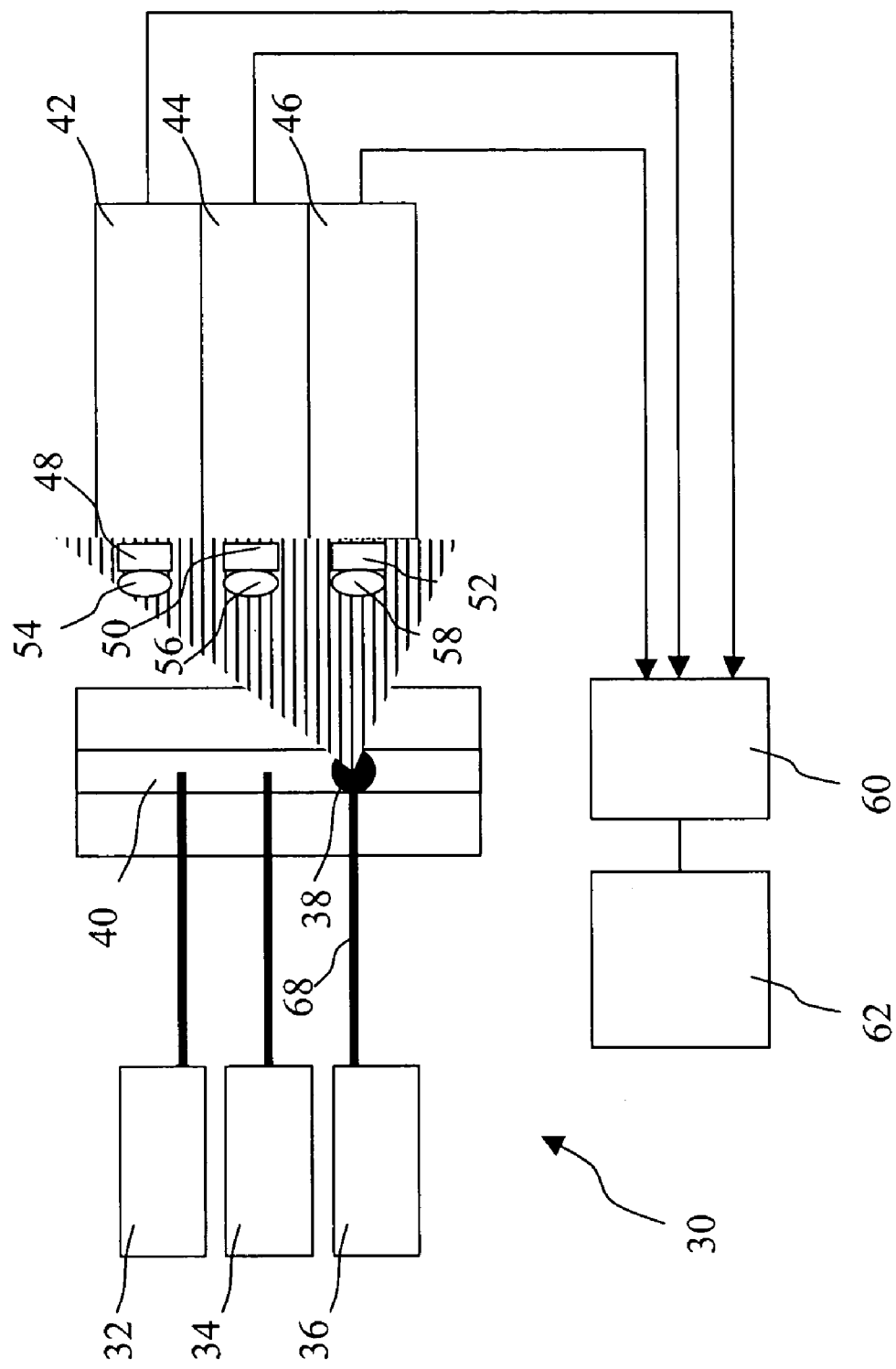
FIG. 6 is a diagram showing the cytometry system of FIG. 2 where a particle is passing through a beam from the third of the three excitation light sources.
Figure 7:
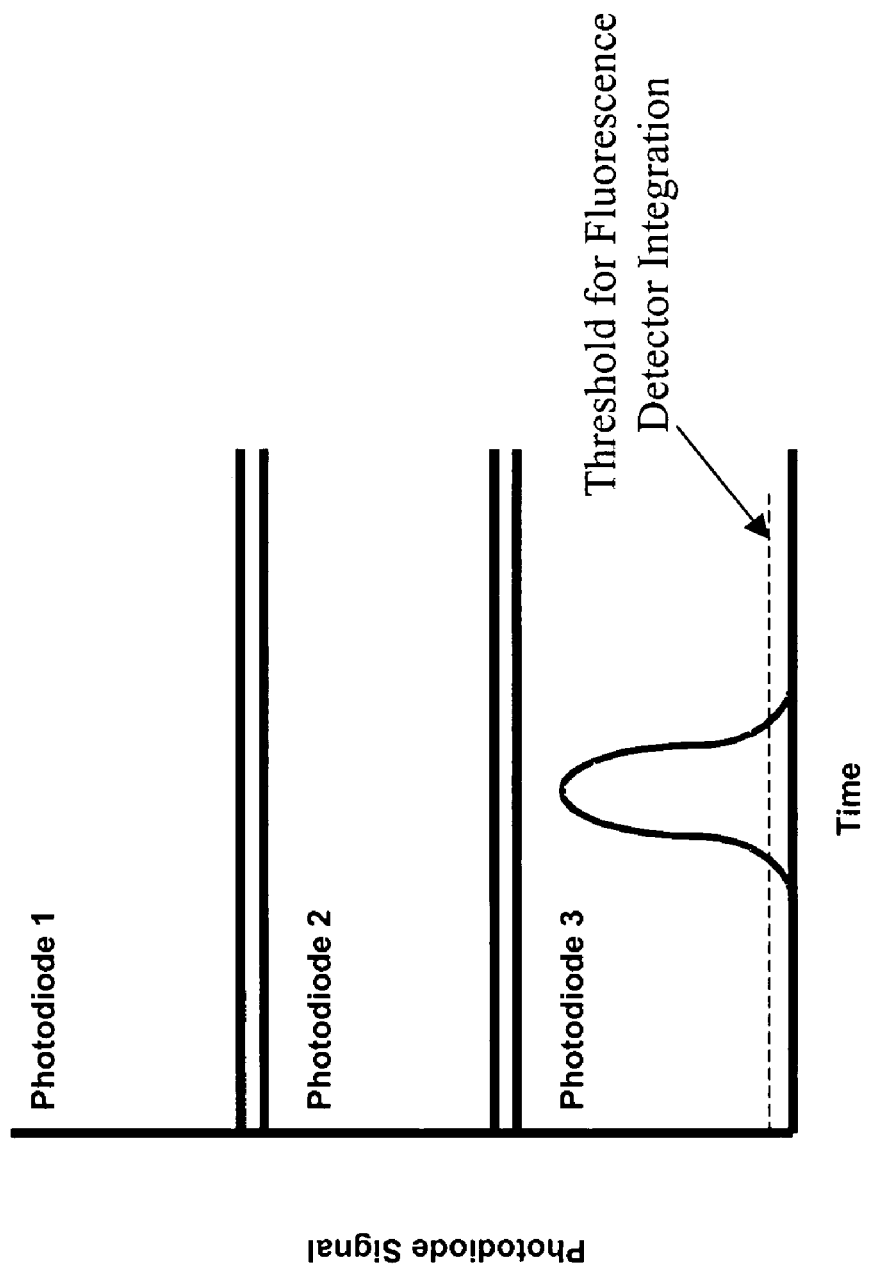
FIG. 7 is a graph showing the signals received from the scatter detectors as illustrated in FIG. 6.

In FIGS. 6 and 7, the particle 38 passes through a beam of light 68 from the third excitation light source 36. The third photodiode 46, which is configured with the third band pass filter 52 to only detect light at the wavelength of the third excitation light source 36, detects scattered light. If the amount of scattered light detected is higher than a preselected threshold, then the trigger 60 triggers the integrators 62 to integrate the signals from the fluorescence detectors associated with the dyes excited by the third excitation light source 36. The first and second photodiodes 42, 44, which are configured to detect scattered light from the first and second excitation light sources 32, 34, do not detect any light.

The excitation light sources need not be focused on different portions of the flow path. Because bandpass filters allow each photodiode to only detect light from one excitation light source, proper trigger of the integrator is possible. When overlap occurs, scattered light is detected by two or more photodiodes, initiating integration at the appropriate fluorescence detectors.

Figure 8:
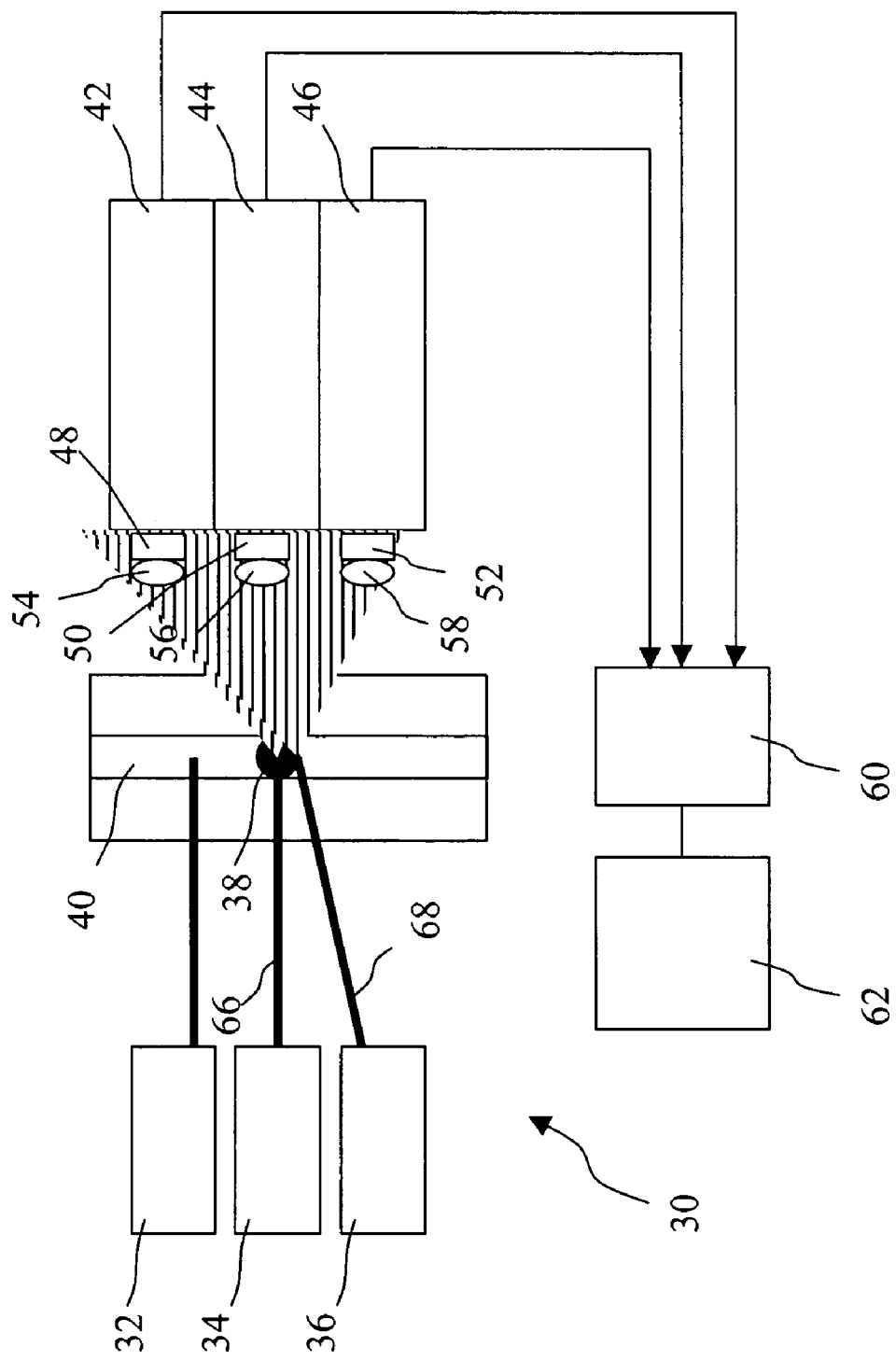
FIG. 8 is a diagram showing a cytometry system employing three excitation light sources according to a first additional embodiment of the present invention where the second and third excitation light sources have slightly different intersection points along the flow path.
Figure 9:
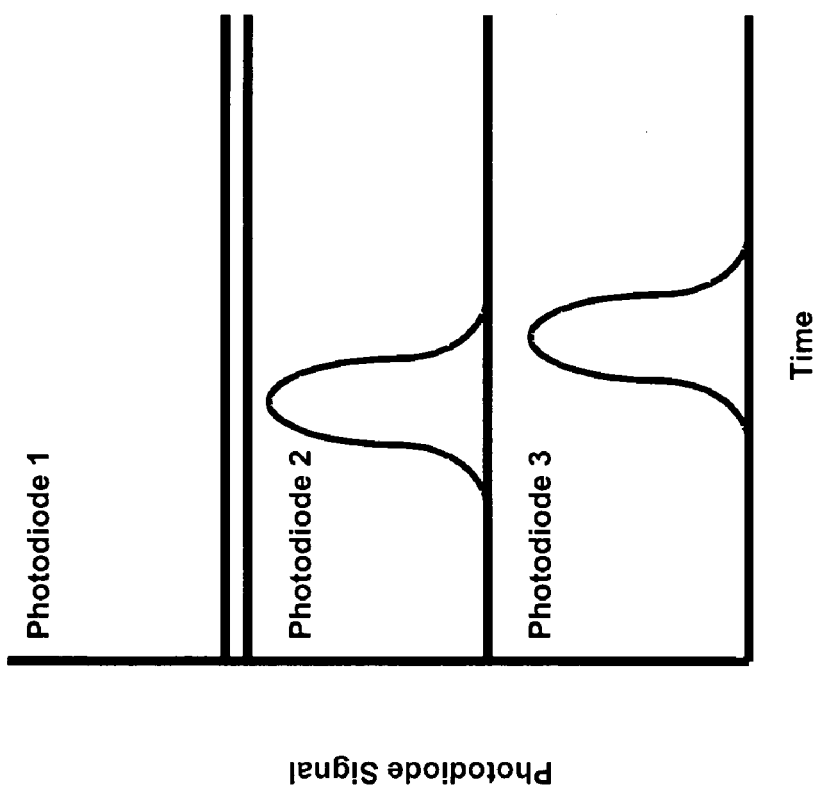
FIG. 9 is a graph showing the signals received from the scatter detectors as illustrated in FIG. 8.

In a first additional embodiment of the present invention, as shown in FIGS. 8 and 9, the particle 38 passes through intersecting beams of light 66, 68 from the second and third excitation light sources 34, 36. The second photodiode 44, which is configured to only detect light at the wavelength of the second excitation light source 34, detects scattered light and triggers integration by the fluorescence detectors associated with fluorescent dyes triggered by the second excitation light source 34.

At the same time, the third photodiode 46, which is configured to only detect light at the wavelength of the third excitation light source 36, detects scattered light and triggers integration by the fluorescence detectors associated with fluorescent dyes triggered by the third excitation light source 36. The first photodiode 42, which is configured to detect scattered light from the first excitation light source 32, does not detect any light and does not trigger integration by its corresponding fluorescence detector.

Preferably, the laser beams are elliptically shaped at the intersection points with the flow path. The aspect ratios of the wide to narrow axes of the elliptical beam are about ten to one with the narrow axis of the ellipse oriented across the axis of flow. The narrow axis is about eight microns and the wide axis is about 80 microns. Preferably, the beams are spaced as close to each other as possible along the flow path without overlapping. The spacing between the beams is preferably about 30 to 50 microns.

Figure 10:
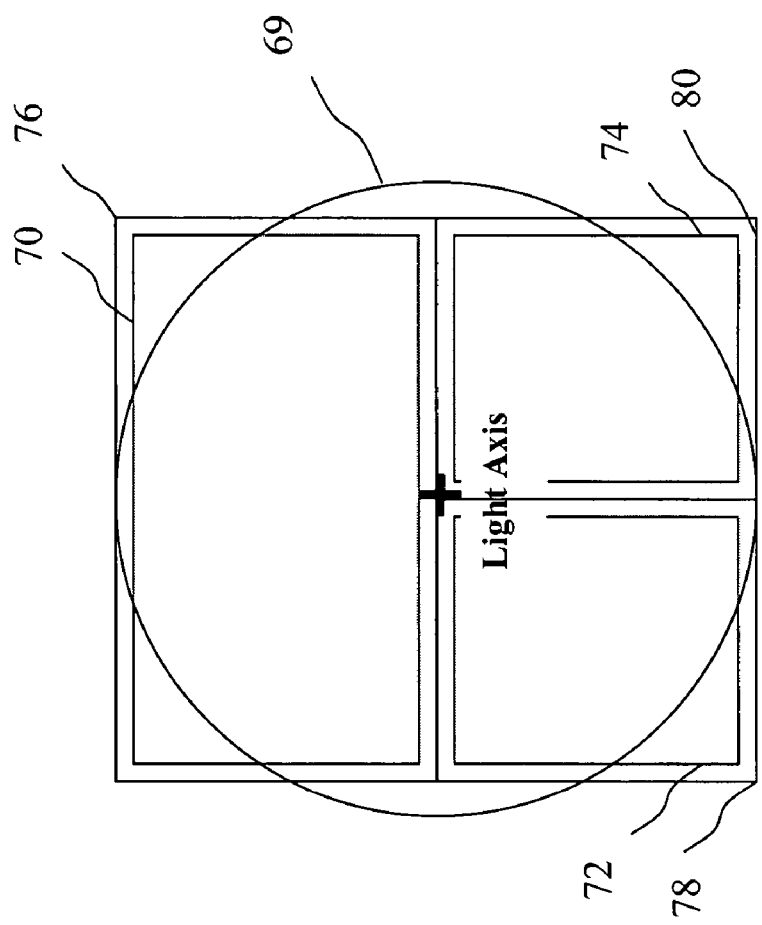
FIG. 10 is a diagram showing placement of scatter detectors according to a second additional embodiment of the present invention.
Figure 11:
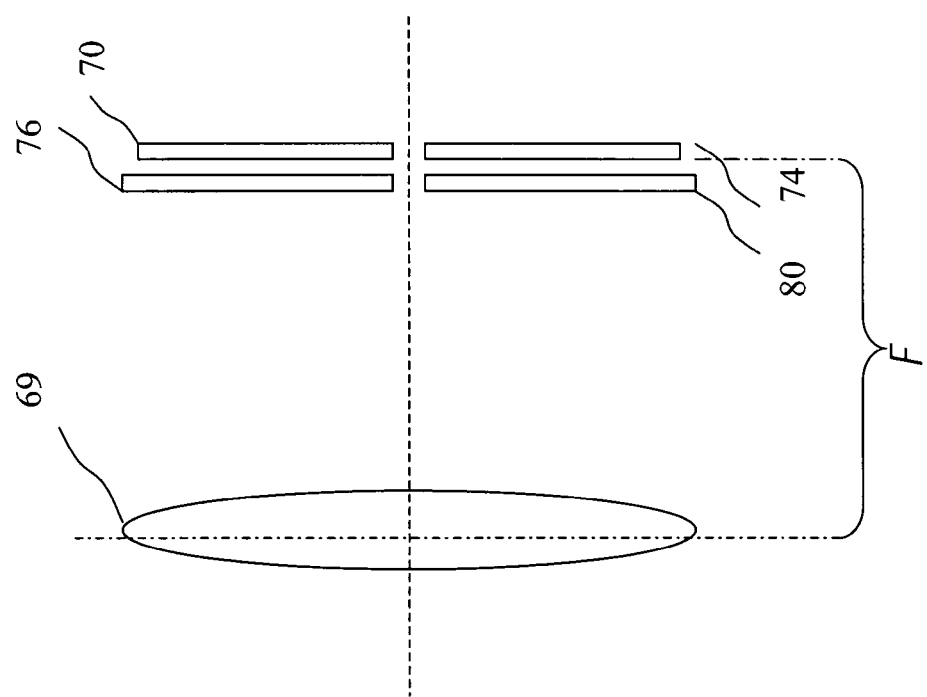
FIG. 11 is a side view of the scatter detectors of the FIG. 10.

FIGS. 10 and 11 show an arrangement of scatter detectors according to a second additional embodiment of the present invention. A single large aperture converging lens 69, acting as a Fourier lens, collects the light scattered from all three of the excitation sources. The laser beams are blocked by a single beam dump (not shown) positioned in front of the lens. Three photodiodes 70, 72, 74 are arranged approximately equidistant from an optical axis of the lens. The photodiodes 70, 72, 74 reside in a plane that is located at one focal length from the lens and is perpendicular to the optical axis of the lens. At the plane of the photodiodes, the optical Fourier transform of the light scattered by the particles is produced. This transform converts intensity of the scattered light versus scattering angle to light intensity versus distance from the optical axis of the lens. This transform is independent of the location of the source. Each photodiode captures light over a large angular range, from about +/−1° to about +/−19°, resulting in an electronic signal which increases monotonically with particle size.

Optionally, one of the photodiodes 70 is approximately twice the area of either of the other photodiodes 72, 74. The difference in area helps compensate for the changing sensitivity of the photodiodes with excitation wavelength. The photodiodes are less sensitive to excitation light in blue wavelengths and increase in sensitivity as the excitation light moves into red and infrared wavelengths. Additionally, the gain of the preamplifiers for the two smaller photodiodes may be adjusted to further compensate for differences in sensitivity. The goal of the adjustment is to obtain approximately the same amplitude signal from each diode for a given size particle.

In front of each photodiode is an optical filter 76, 78, 80 allowing only one of the three excitation light wavelengths to reach the photodiode. The output from each photodiode detector 70, 72, 74 may be fed into a separate signal processing board acting as a trigger (not shown) so that each signal can act as an independent trigger. Additionally, the output signals from all three photodiodes 70, 72, 74 may be summed together and the resulting composite signal fed into a single scope channel for display.

Each signal processing board tests the output from the photodiode to determine whether the output has reached a predetermined trigger level. If the output from the photodiode is higher than the predetermined trigger level, then the signal processing board instructs an integrator (not shown) to integrate the signal received from the appropriate fluorescence detectors.

Once triggered, the integrator may integrate any detected signal for a preselected minimum time period. The signal processing board continues to test the output from the triggering photodiode until the output falls below the predetermined trigger level. Once the output from the triggering photodiode falls below the predetermined trigger level, the signal processing board instructs the integrator to cease integrating.

Figure 12:
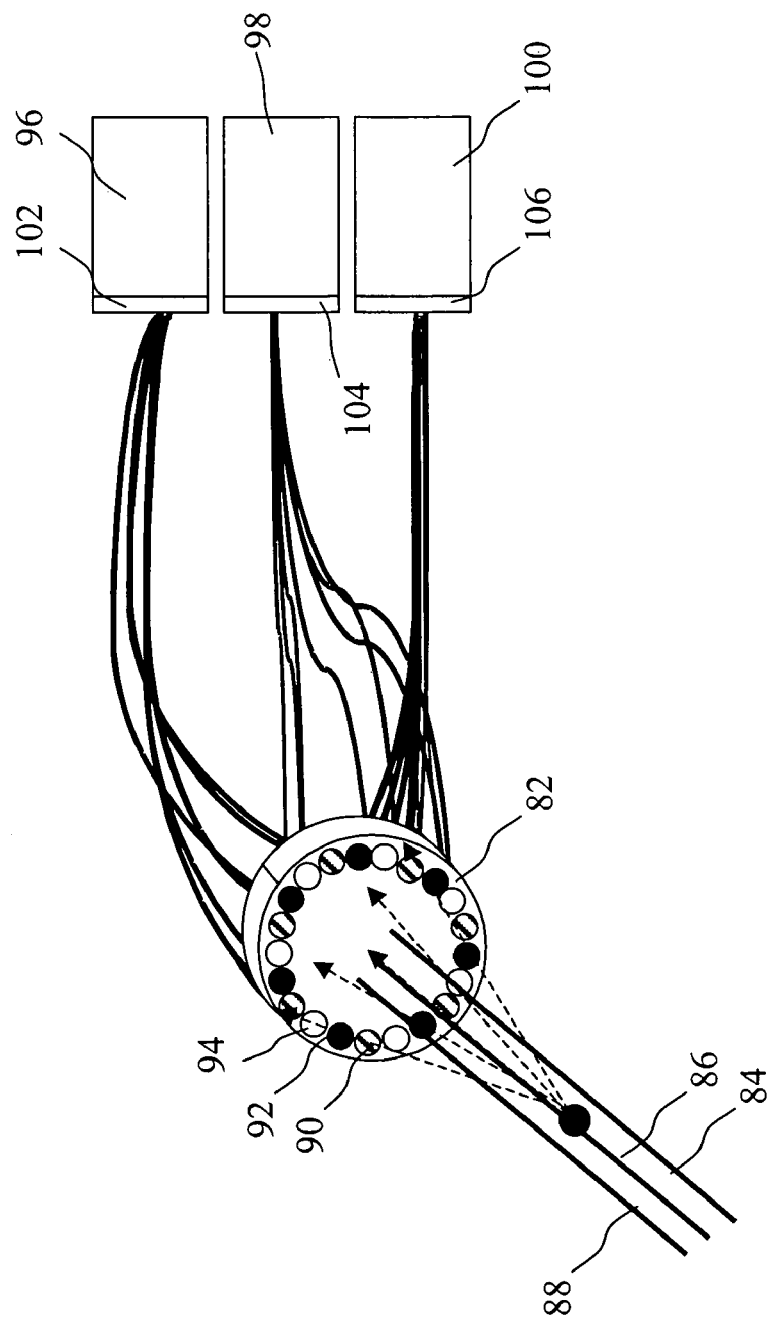
FIG. 12 is a diagram showing placement of scatter detectors according to a third additional embodiment of the present invention.

In a third additional embodiment of the present invention, as shown in FIG. 12, a fiber optic bundle 82 is used to form the scatter detectors. Three lasers 84, 86, 88 are used as excitation light sources. The fiber optic bundle 82 contains three different sets of fibers 90, 92, 94. Each of the three sets of fibers 90, 92, 94 corresponds to one of the three lasers 84, 86, 88. Each of the three sets of fibers 90, 92, 94 is directed to a separate photodiode 96, 98, 100. Each of the three photodiodes 96, 98, 100 is responsible for detecting light from one of the three lasers. The photodiodes may be used with or without a Fourier lens.

Each photodiode 96, 98, 100 has a bandpass filter 102, 104, 106 in front of it to allow only one wavelength of light to be transmitted to the photodiode 96, 98, 100. As shown in FIG. 12, the fiber optic bundle 82 may be arranged so that every third fiber is a member of the same set and addresses the same photodiode. Because the relative position of the excitation light sources is known, small drifts in excitation light source position between experiments may be tolerated.

The present invention also allows for a reduced number of fluorescence detectors. Typically, a separate fluorescence detector is employed for each different dye to be detected. Each fluorescence detector has a filter in front of it allowing only light having a wavelength of a specific dye to pass.

Typically, in a system with two different excitation light sources where each excitation light source excites two different dyes on a particle, four different fluorescence detectors are needed. When a particle passes in front of the first excitation light source, two fluorescence detectors associated with the dyes excited by the first excitation light source begin integrating. Similarly, when the particle passes in front of the second excitation light source, the two fluorescence detectors associated with the dyes excited by the second excitation light source begin integrating.

The present invention uses scatter detectors specific to each excitation light source to know which excitation light source is interrogating a particle at a given time. Additionally, the present invention uses multi-band pass filters in conjunction with each fluorescence detector to reduce the number of fluorescence detectors necessary.

Figure 13:
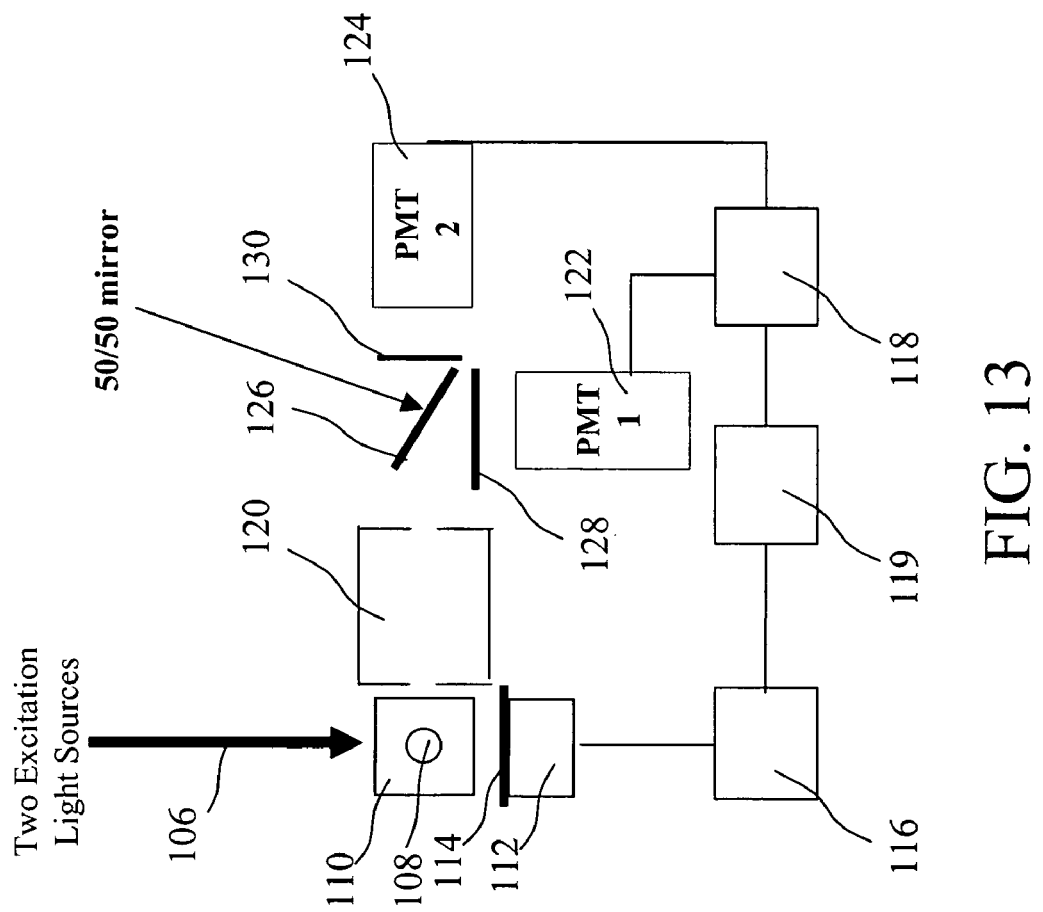
FIG. 13 is a diagram of a flow cytometry system employing multiple excitation light sources according to a fourth additional embodiment of the present invention.

A fourth additional embodiment of the present invention is shown in FIG. 13. As shown in FIG. 13, an exemplary system employing multi-band-pass filters in conjunction with fluorescence detectors has two excitation light sources 106 focused on a particle 108 in a flow path 110. In this exemplary embodiment, the two excitation light sources are lasers. One laser has a wavelength of 532 nm and the other laser has a wavelength of 635 nm. Two photodiodes 112, each coupled to a separate band pass filter 114 corresponding to one of the two laser wavelengths, are positioned to receive scattered excitation light. Each photodiodes is electrically coupled to a trigger 116 which is electrically coupled to an integrator 118. Optionally, a controller 119 is coupled to the triggers 116 and the integrators 118. Note that in FIG. 13, the flow path 110 is oriented perpendicular to the page. Therefore, only one of each of the two excitation light sources 106, photodiodes 112, band pass filters 114, triggers 116, and integrators 118 are visible.

Fluorescence emitted by the dyes associated with the particle are collected by fluorescence collection optics 120. A first photomultiplier tube 122 and a second photomultiplier tube 124 are used as fluorescence detectors. The first and second photomultiplier tubes 122, 124 are electrically coupled to the integrators 118 and are positioned at 90 degrees to each other around a 50/50 mirror 126. The 50/50 mirror 126 is designed to reflect 50% of the light incident upon it and to transmit 50% of the light incident upon it.

The first photomultiplier tube 122 is coupled to a first dual bandpass filter 128. The second photomultiplier tube 124 is coupled to a second dual band pass filter 130. Each dual bandpass filter 128, 130 is designed to pass light emitted from one dye excited by each of the two lasers.

In this exemplary embodiment, each particle has three dyes: phycoerythrin (PE), emitting at 575 nm and 605 nm in response to excitation by 532 nm light, BCD646, a squaraine dye emitting at 660 nm in response to excitation by 635 nm light, and BCD676, a cyanine dye, emitting at 780 nm in response to excitation by 635 nm light. Other dyes may be substituted for those listed above as will be understood by those skilled in the art.

The first dual band pass filter 128 passes 575 nm light arising from 532 nm excitation and 660 nm light arising from 635 nm excitation. The second dual band pass filter 130 passes 605 nm light arising from 532 nm excitation and 780 nm light arising from 635 nm excitation. Other excitation light source/emission combinations are possible, as will be recognized by those skilled in the art.

The lasers are spatially offset from each other by manually or automatically repositioning the lasers and monitoring the two forward scatter sensing photodiodes. The lasers are spatially offset when the signals from the two photodiodes 112 do not coincide in time.

Because the photodiodes indicate which laser is currently illuminating the particle, the response from each photomultiplier tube may be assigned to a particular dye. For illustrative purposes, the particle first addresses the 532 nm laser and then the 635 nm laser. However, as will be appreciated by those skilled in the art, the order need not be known prior to usage.

When the photodiode with the 532 nm bandpass filter detects a response, the particle 108 is in front of the 532 nm laser. The dye being addressed is PE, emitting at 575 nm and 605 nm. Fluorescence from these two channels will dominate the emission. The output from both the first and second photomultiplier tubes is integrated and assigned to PE.

As the particle 108 continues to flow down the flowpath 110, the particle reaches the 635 nm laser and the photodiode with the 635 nm bandpass filter triggers integration of the signal from the photomultiplier tubes. The two dyes being addressed are now BCD646 and BCD676. The output from the first photomultiplier tube is assigned to BCD646 and the output from the second photomultiplier tube is assigned to BCD676. In effect, the scatter sensing photodiodes in combination with the fluorescence detectors allows the integration information from each photomultiplier tube to be dynamically assigned based on which laser is interrogating the particle.

When a particle crosses the path of an excitation light, scatter occurs in multiple directions from the particle. Although forward angle light scatter predominates, a significant amount of scatter occurs orthogonal to direction of the excitation light.

Figure 14:
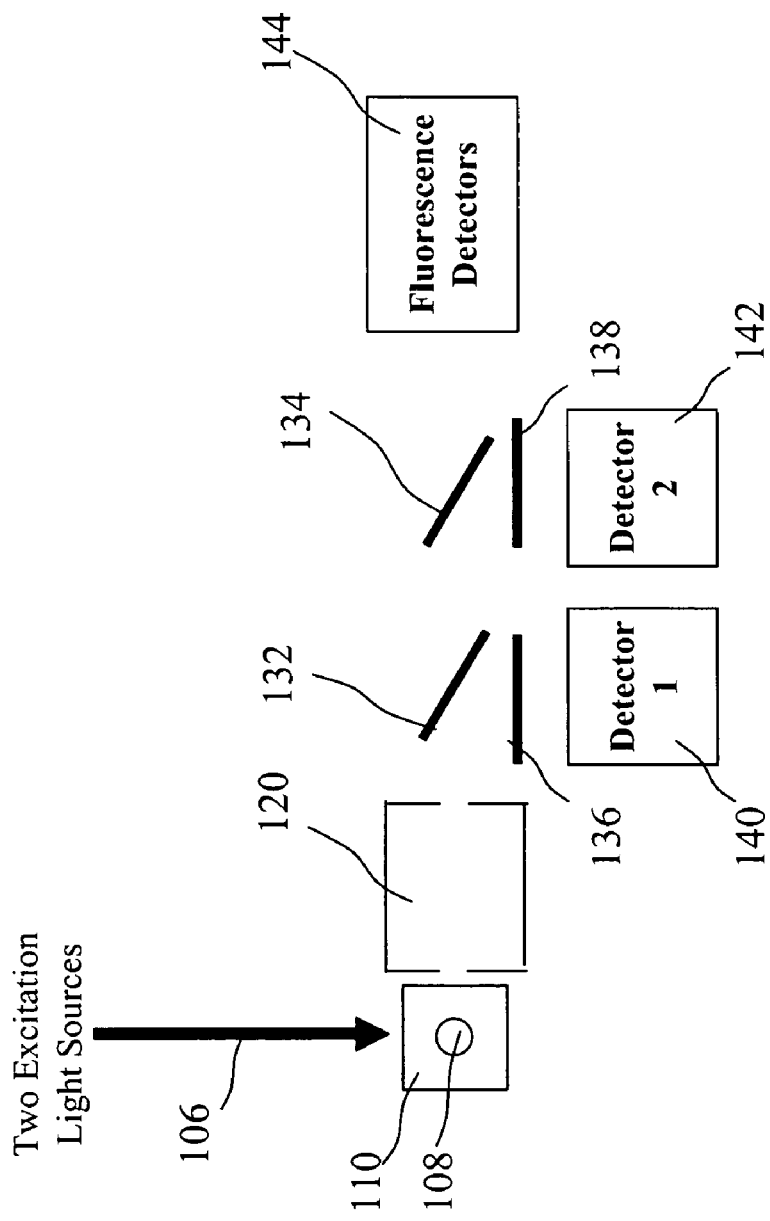
FIG. 14 is a diagram of a flow cytometry system employing multiple excitation light detectors positioned as side scatter detectors according to a fifth embodiment of the present invention.

In a fifth additional embodiment, as shown in FIG. 14, scatter detectors are arranged to collect side scattered light. In this embodiment, there are two excitation sources, such as lasers. Excitation light 106 is focused on a particle 108 in a flow path 110. Side scatter and fluorescence emitted by the dyes associated with the particle are collected by fluorescence collection optics 120. Note that in FIG. 14, the flow path 110 is oriented perpendicular to the page. Therefore, only one of the two excitation light sources 106 is visible.

A first piece of glass 132, arranged at about 45 degrees relative to the path of light exiting the collection optics, reflects a small amount of light, such as approximately 4%. The reflected light passes through a first optical filter 136 designed to transmit the light from only one of the two lasers. The reflected light passed through the first optical filter 136 is then detected by a first photodetector 140, such as a photomultiplier tube or photodiode.

The light that is transmitted though the first piece of glass 132 strikes a second piece of glass 134 arranged at about 45 degrees relative to the path of the light exiting the collection optics. The second piece of glass 134 reflects a small amount of light, such as approximately 4%. The light reflected from the second piece of glass 134 passes through a second optical filter 138, designed to transmit the light from the other laser. The reflected light passed through the second optical filter 138 is then detected by a second photodetector 142, such as a photomultiplier tube or photodiode.

The outputs from the first and second photodetectors 140, 142 are sent to signal processing boards that serve as triggers for integrators (not shown) coupled to fluorescence detectors 144 associated with each laser. Optionally, a controller (not shown) is coupled to the signal processing boards and the integrators.

The present inventive concept can be extended to larger numbers of monitored dyes. If X is the maximum number of dyes excited by any one laser in the system, then X detectors will be required, with the filters in front of each detector containing a maximum of Y bandpass regions, where Y is the number lasers. As an example, if there are a total of 15 dyes and three lasers, with five dyes being excited by each laser, then five detectors may be used, with each detector being coupled to a multi-bandpass filter having three bandpasses.

Although this invention increases the range over which lasers can be aligned to obtain good fluorescence information, the range is limited. The limitation is primarily due to the viewing region of the fluorescence collection optics. Typically, the fluorescence collection optics collect the fluorescent emission from a particle, focus the fluorescent emission though a pinhole several hundred microns wide, and then collimate fluorescent emission to the fluorescence detector. The pinhole is present to spatially filter out scattered light. If the excitation light sources are moved so that the fluorescence light is beyond the range that the optics can collect and transmit through the pinhole, then the collection efficiency drops, reducing the fluorescence intensity. This limitation may be somewhat reduced by replacing the pinhole with a vertical slit. The range that the optics can collect and transmit is then extended along the flow of the particles.

If certain conditions are not controlled when independent triggers from spatially separated excitation light sources are used, anomalous data may be acquired. There are several sources for these anomalies that can be controlled by a controller that processes signals from the triggers in order to assure accurate data.

A first source of anomalous data results when a trigger signal is generated from one of the excitation light sources but not from any number of the other excitation light sources. This can occur when the signal received by one trigger from its corresponding scatter detector is of sufficient amplitude to cross the predetermined threshold value, but the signals from all scatter detectors are insufficient to cross their respective predetermined threshold values. A first method of preventing the first source of anomalous data is to maintain the trigger threshold values as low as possible with respect to the scatter detector signal amplitude. However, this approach is limited, because the predetermined threshold values should also be kept above the background noise level so as to prevent spurious trigger signals from debris, optical noise, and electronic noise.

A second method of preventing the first source of anomalous data is to require a scatter detector signal of sufficient amplitude to cross the first trigger threshold value in order to initiate an "event" and then to enable subsequent triggers using the "event" signal. With this method, there should also be a time out means, which limits the duration of the "event" if one or more of the subsequent trigger threshold values are not crossed. In a simple implementation, a single time-out means is initiated by the beginning of an "event" and reaches a terminal count slightly after the expected end of the "event" if all of the required triggers have not occurred.

In a more complex implementation, the time out means should be set to a period of time slightly longer than the expected time between two sequential triggers and should force a trigger if one has not occurred. In a system with multiple independent triggers, this time out means should be reset and rearmed between each pair of potential independent triggers. This implementation allows identification of which trigger was missing. In either implementation, the forcing of the trigger function maintains the integrity of the capture and acquisition cycles. Any data frame containing a forced trigger should be marked indicating that frame may contain suspect data and should not be included in the final data set.

A second source of potentially anomalous data is the presence of a second particle traveling near the particle from which data is being acquired. This problem increases in severity as the frequency of the sample particles increases. Because of the cycle time of the capture process there is a finite distance between two sequential events within which both of the two events cannot be captured, this is the "busy" time. This "busy" time results in all "events" being divided into two classes: "events" that are captured and "events" that are missed. Not only is no data recorded about a "missed event", but it can also contaminate the data from a "captured event" if some portion of the signal from a "missed event" falls within the capture window for a "captured event".

Contaminating "missed events" fall into two classes; those that precede a "captured event" and those that follow a "captured event". The preceding "missed events" are events that occur during the "busy" time of an earlier occurring "captured event". If the capture system, including the trigger(s) and integrator(s), has finished capturing an event and is ready to be rearmed, then a determination should be made that there is not another event already in progress. If the capture system becomes rearmed during an event, then the position of the sample particle cannot be accurately determined and data concerning that particle cannot be accurately captured. Therefore, the rearming process should test the trigger signal(s) to verify that an event is not in process.

If the capture system is rearmed immediately after a "missed event" ends and is then triggered by a closely following next event, both events may be present within the capture window. One method of preventing this problem is to hold off the rearming of the capture process by a time period that extends beyond the end of the leading event by a preselected delay time period. The preselected delay time period may be, for example, equal to about half of the capture window width. Every event resets and restarts the delay time period.

To detect and compensate for contamination by a following "missed event", the capture system examines the trigger processor for additional events during the "busy" period. If additional events occur, then the "captured event" is marked as potentially contaminated and should not be included in the final data set.

A third source of potentially anomalous data is the presence of a "missed event" particle traveling far enough from the captured particle to not appear in the same capture window, but preceding close enough to the captured particle to trigger the next trigger early. To reduce this possibility, the time out means described above is modified to provide an enabling window that brackets the time of the expected trigger. This discriminates against early triggering while permitting the trigger to depend on the signal from the captured particle. If the enabling window ends and a trigger has not occurred, than the first trigger is forced as described above to maintain correlation. Any data frame containing a forced trigger should be marked indicating that frame may contain suspect data and should not be included in the final data set.

A final source of potential contamination of "captured events" is when there is overlap in the capture windows for two events, which are in the capture process, but are at different laser positions. The probability of this potential problem increases as the number of laser interrogation points increases, the distance between the interrogation points increases, and as the sample particle rate increases. The severity of this problem is dependent upon the degree of optical isolation between the different optical measurement channels. The fact that overlap has occurred between two or more capture windows is detectable and can be used to flag possibly anomalous results.

All of these potential causes of incorrect capture should be detected and controlled by the electronics that process the trigger signals in order to prevent anomalous data from being acquired.

The present invention eliminates the need for the light beams from two or more excitation light sources to intersect a single point in a flow cell. Additionally, the present invention reduces interfering fluorescence from dyes excited by other excitation light sources ("crosstalk"). Additionally, overall alignment of excitation light sources is less restrictive, because each excitation light source has its own positional sensor. The use of multi-bandpass filters in conjunction with fewer photomultiplier tubes and associated electronics results in significant cost and space savings.

Although the present invention has been described in considerable detail with reference to certain preferred versions thereof, other versions are possible. Therefore, the spirit and scope of the appended claims should not be limited to the description of the preferred versions described herein.

All features disclosed in the specification, including the claims, abstracts and drawings, and all the steps in any method or process disclosed, may be combined in any combination except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. §112.

The invention claimed is:

1. A method for measuring the fluorescence of a particle having a plurality of dyes, the method comprising:
   a) interrogating a particle with a first excitation light source;
   b) detecting the interrogation of the particle with the first excitation light source using a scatter detector configured to only detect light from the first excitation light source;
   c) detecting any fluorescence emitted by the particle using a fluorescence detector when it is detected that the particle is being interrogated by the first excitation light source;
   d) interrogating a particle with a second excitation light source;
   e) detecting the interrogation of the particle with the second excitation light source using a scatter detector configured to only detect light from the second excitation light source; and
   f) detecting any fluorescence emitted by the particle using the fluorescence detector when it is detected that the particle is being interrogated by the second excitation light source; and
   dynamically assigning fluorescence detected in steps c) and f) to specific ones of the plurality of dyes depending on the excitation light sources.

2. A system for measuring the irradiance of a particle labeled with a plurality of fluorescent labels, consisting essentially of:
   a cytometric flow chamber having a flow path for passage of the fluorescently labeled particle;
   a plurality of excitation light sources, each emitting a beam of light incident on the cytometric flow chamber;
   a plurality of scatter detectors in optical communication with the flow path of the cytometric flow chamber, each configured to detect light from only one of the plurality of excitation light sources and arranged so as to detect scattered light from the fluorescently labeled particle as it passes through the flow path of the cytometric flow chamber;
   a plurality of triggers, each of the plurality of triggers being coupled to a separate corresponding one of the plurality of scatter detectors, and each trigger emitting a signal when scattered light incident on the corresponding scatter detector exceeds a predetermined threshold value;
   collection optics in optical communication with the flow path of the cytometric flow chamber to collect emissions from the fluorescently labeled particle;
   a plurality of fluorescence detectors to receive the emissions collected by the collection optics and generate an output, each of the fluorescence detectors being configured to respond only to a discrete number of wavelength bands; and
   a plurality of integrators, each integrator being coupled to a separate corresponding one of the plurality of triggers, and each integrator being configured to record the output of at least one of the plurality of fluorescence detectors in response to a signal from the corresponding trigger;
   wherein each of the plurality of integrators is controlled only by a separate one of the plurality of triggers in response to scattered light incident on one of the scatter detectors; and
   wherein the output of each integrator is dynamically assigned to one of the fluorescent labels depending on which laser is interrogating the particle.

3. The system of claim 2 further comprising a controller coupled to the plurality of integrators and the plurality of triggers, the controller being programmed to control the plurality of integrators and the plurality of triggers to prevent anomalous data from being acquired.

4. The system of claim 2 wherein:
   the excitation light sources are positioned about an excitation light axis;
   a fiber optic bundle is configured around the excitation light axis, the fiber optic bundle containing a plurality of sets of optical fibers; and
   each set of optical fibers is optically coupled to a different one of the scatter detectors.

5. The system of claim 2 wherein at least two excitation light sources are focused to overlap in the flow path of the flow chamber.

6. The system of claim 2 wherein each of the plurality of scatter detectors further comprises a photodiode.

7. The system of claim 2 wherein at least one fluorescence detector comprises a photomultiplier tube.

8. The system of claim 2 wherein at least one of the plurality of excitation light sources comprises a laser.

* * * * *